(12) United States Patent
Villani et al.

(10) Patent No.: US 8,182,449 B2
(45) Date of Patent: May 22, 2012

(54) KIT FOR PARENTERAL ADMINISTRATION OF MEDICAMENTS

(75) Inventors: Flavio Villani, Parma (IT); Paolo Magri', Corteglia (CH)

(73) Assignee: INFA, S.A., Mendrisio (CH)

( * ) Notice: Subject to any disclaimer, the term of this patent is extended or adjusted under 35 U.S.C. 154(b) by 91 days.

(21) Appl. No.: 11/992,405

(22) PCT Filed: Sep. 29, 2006

(86) PCT No.: PCT/IB2006/002702
§ 371 (c)(1),
(2), (4) Date: May 27, 2008

(87) PCT Pub. No.: WO2007/036792
PCT Pub. Date: Apr. 5, 2007

(65) Prior Publication Data
US 2009/0264830 A1    Oct. 22, 2009

(30) Foreign Application Priority Data

Sep. 29, 2005 (IT) .................. MI2005A1826

(51) Int. Cl.
| | |
|---|---|
| *A61M 5/00* | (2006.01) |
| *A61M 25/00* | (2006.01) |
| *A61B 19/00* | (2006.01) |
| *A61K 9/20* | (2006.01) |

(52) U.S. Cl. ........ 604/187; 604/181; 604/191; 604/264; 604/403; 604/416; 424/465

(58) Field of Classification Search .................. 604/187, 604/191, 264, 416, 413, 403; 549/510; 424/465
See application file for complete search history.

(56) References Cited

U.S. PATENT DOCUMENTS

| | | | | |
|---|---|---|---|---|
| 3,730,338 | A  * | 5/1973  | Chesky ....................... | 206/459.5 |
| 6,232,477 | B1 * | 5/2001  | Bouchard et al. ............. | 549/510 |
| 6,645,181 | B1 * | 11/2003 | Lavi et al. .................... | 604/191 |
| 7,488,309 | B2 * | 2/2009  | Kissinger et al. ............. | 604/246 |
| 2002/0013340 | A1 | 1/2002 | Peyman | |
| 2002/0192280 | A1 * | 12/2002 | Hunter et al. ................. | 424/465 |
| 2004/0234472 | A1 | 11/2004 | Jackson et al. | |

FOREIGN PATENT DOCUMENTS

| | | |
|---|---|---|
| EP | 1 070 502 | 1/2001 |
| GB | 2 388 025 | 11/2003 |
| GB | 2388025 | * 11/2003 |
| GB | 2388025 A | * 11/2003 |
| WO | 01/28522 | 4/2001 |
| WO | 2004/043390 | 5/2004 |

OTHER PUBLICATIONS

Venkataramanan et al., "Leaching of diethylhexylphthalate from polyvinyl chloride bags into intravenous cyclosporine solution", *American Journal of Hospital Pharmacy*, vol. 43, Nov. 1986, pp. 2800-2802, XP008079824.

Waugh et al., "Stability, compatibility, and plasticizer extraction of taxol (NSC-125973) injection diluted in infusion solutions and stored in various containers", *American Journal of Hospital Pharmacy*, vol. 48, Jul. 1991, pp. 1520-1524, XP000874878.

Allwood et al., "The extraction of diethylhexylphthalate from polyvinyl chloride from components on intravenous infusion containers and administration sets by paclitaxel injection", *International Journal of Pharmaceutics*, vol. 127, 1996, pp. 65-71.

* cited by examiner

*Primary Examiner* — Kevin C Sirmons
*Assistant Examiner* — Bradley Thomas, Jr.
(74) *Attorney, Agent, or Firm* — Nixon & Vanderhye PC

(57) ABSTRACT

The invention relates to a kit for parenteral administration of drugs, particularly a kit for the infusion of those medicaments dissolved in solvents that extract toxic components from PVC, which is also suitable for the infusion of highly active medicaments, said kit ensuring a safe administration both for the patient and for healthcare staff.

7 Claims, 1 Drawing Sheet

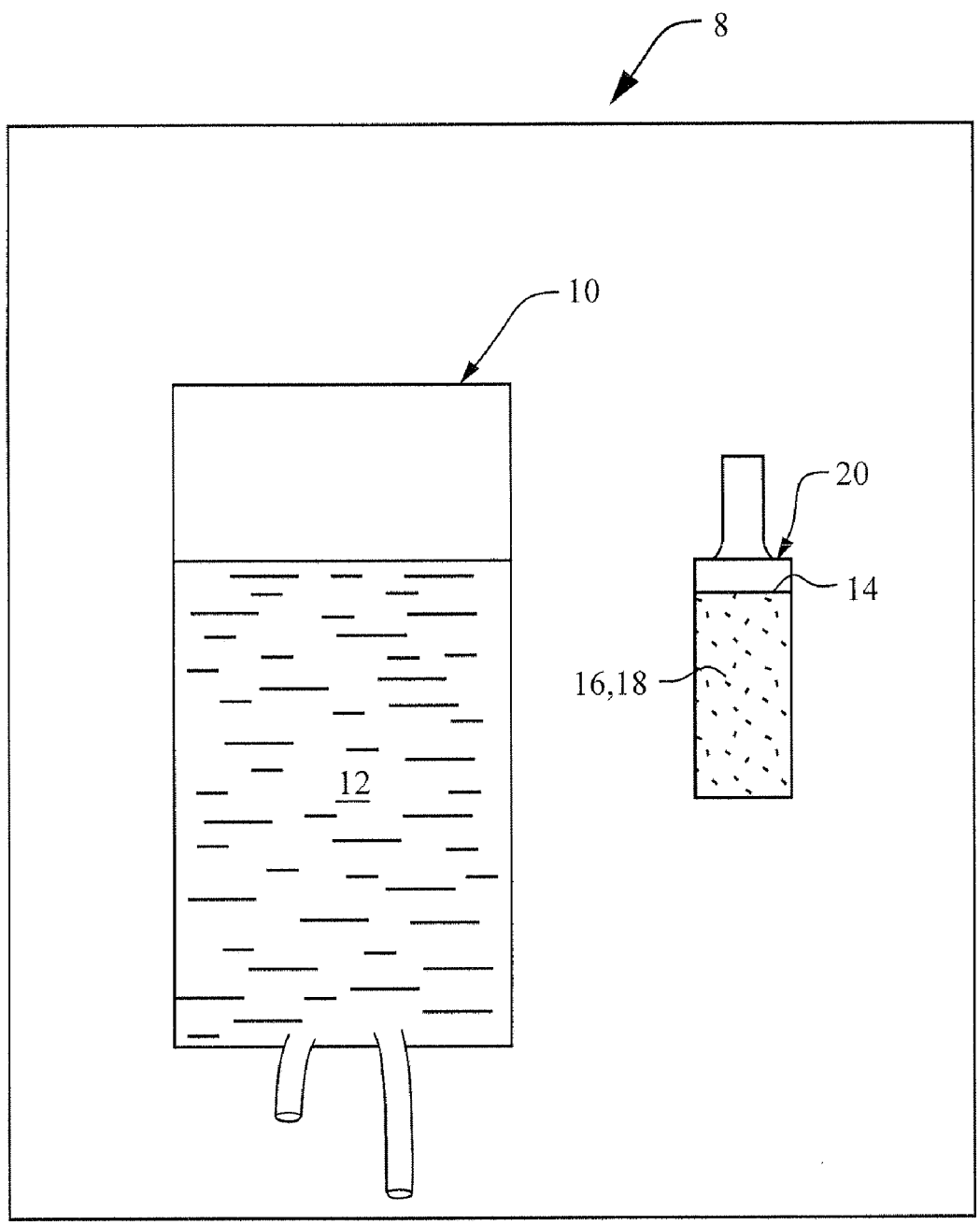

KIT FOR PARENTERAL ADMINISTRATION OF MEDICAMENTS

This application is the U.S. national phase of International Application No. PCT/IB2006/002702 filed 29 Sep. 2006 which designated the U.S. and claims priority to Italian Patent Application No. MI2005A001826 filed 29 Sep. 2005, the entire contents of each of which are hereby incorporated by reference.

FIELD OF THE INVENTION

The present invention relates to a kit for parenteral administration of medicaments. Particularly, the subject-matter of the invention is a kit for the infusion of those medicaments dissolved in solvents that extract toxic components from PVC, said kit being also suitable for the infusion of highly active medicaments, and ensuring a safe administration both for the patient who receives them and for the healthcare staff administering said medicaments.

BACKGROUND OF THE INVENTION

Several highly active ingredients, such as antitumoral agents, immunosuppressors, antivirals, several hormone derivatives, are deemed as being potentially dangerous for the healthcare staff who is required to handle them upon administration. To the purpose, in the United States, the NIOSH (National Institute for Occupational Safety and Health) issued some directives to safeguard the health and safety of healthcare personnel (www.cdc.gov/niosh) and listed the dangerous active ingredients for which particular care should be taken upon administration, such as using gloves and glasses when the drug package (vial or the like) is being opened, etc.

In a number of cases, the administration of many drugs is carried out intravenously, either because of the inherent characteristics of the active ingredient, or when the patient's conditions are such that oral administration is not practicable; when, as sometimes happens, the therapy is chronic, the patient is regularly subjected to intravenous infusions, even for several months.

Water is the preferred medium used in injectable drugs, but unfortunately it cannot be used with all drugs, due to its chemical-physical incompatibility with several active ingredients. Some of the latter, in fact, prove to be either insoluble or instable in water and are necessarily formulated with lipophilic solvents, such as vegetable oils, such as castor oil, olive oil or organic solvents and surfactants, such as ethanol, benzyl alcohol, polyethylene glycols (PEG), polysorbates (such as polysorbate 80 or Tween80®), etc.

It has been found that the use of lipophilic mediums is incompatible with several plastic materials used for intravenous administration, particularly with conventional PVC (polyvinyl chloride) from which said solvents may extract phthalates, particularly di(2-ethylhexyl)phthalate (DEHP), i.e. fat-soluble compounds that are very toxic to the organism.

For these reasons, common infusion bags for intravenous administration must not be used with the injectable active ingredients formulated in lipophilic mediums, but rather infusion bags have to be selected which are made of inert plastic material, such as polyethylene (PE), polypropylene or other polyolefins or alternatively glass bottles.

This incompatibility is reported in the instructions written on the information leaflets that are attached to packages of drugs injectable by infusion formulated in several mediums, such as tacrolimus (Prograf®), cyclosporine (Sandimmun®) taxanes (e.g. docetaxel—Taxotere® and paclitaxel—Taxol®). It is understood, however, that there is a non-remote chance that, by mistake, due for example to hurry, distraction, incompetence by the healthcare staff responsible for preparing the infusion bag, these instructions are not clearly understood and a vial containing the active ingredient in the lipophilic solvent is inadvertently administered in a conventional PVC bag, with clear dangerous consequences for the patient receiving the infusion and consequent serious charges against the healthcare staff.

The present invention aims at overcoming these drawbacks by providing a kit for administering drugs formulated in lipophilic solvents by the parenteral, advantageously intravenous, route, which provides a healthcare operator in charge of treating a patient with all the material required, in order to prevent any risk deriving from mistakes, negligence or incompetence.

BRIEF DESCRIPTION OF THE DRAWINGS

A kit for the parenteral administration of drugs is shown.

DESCRIPTION OF THE INVENTION

Therefore, according to one of the aspects of the present invention, the subject-matter of invention is a kit 8 for the parenteral administration of drugs formulated in lipophilic solvents, comprising:
  a) at least one vessel 10 containing a fluid 12 for parenteral infusion;
  b) at least one dosage unit 14 comprising at least one drug 16 formulated in a lipophilic solvent 18 to be administered by the parenteral route;
  c) at least one means 20 for delivering the drug from the dosage unit 14 to the vessel 10;
the vessel 10, dosage unit 14 and means 20 being made of materials compatible with the lipophilic solvents.

By "parenteral administration" is meant, according to the present invention, any administration by a route other than oral, and mainly, though not exclusively, includes intravenous administration.

The "vessel" such as in component (a) is for example an infusion bag, flask or bottle, and contains a "fluid for parenteral infusion", which is either a solution or microemulsion for infusion, such as a physiological solution containing salts, sugars, etc., or a microsuspension such as of the type for parenteral nutrition, all the above being advantageously sterile.

According to a preferred embodiment of the present invention, the "vessel" can be a flask, a bag or a bottle or a flask made of special non PVC-containing plastic material, or at least with an inert inner polyethylene layer, or alternatively made of glass.

According to a particularly preferred embodiment, the vessel is a bottle or a flask made of the required quality of plastic as above, but which is also collapsible and preferably that can also be environmentally friendly when disposed.

The "vessel" of the invention further comprises connectors, cannulae, flow regulators, optional filters or dosers, and all the material for delivering the fluid by parenteral infusion, advantageously by intravenous infusion, such as needles, butterfly valve, etc.

The drug formulated in a lipophilic solvent in (b) is packaged in suitable dosage units, such as for example ampoules, vials or bottles, vials and more particularly glass vials, being preferred.

According to the present invention, by "means for delivering the drug" is meant any tool suitable to deliver the drug from the dosage unit (b) to the vessel (a) and for example includes the syringes; alternatively, the means for delivering the drug may consist of a suitable connector, which communicates said dosage unit with said vessel.

According to a preferred embodiment of the invention, suitable connectors are those ensuring a truly effective transfer of the drug in the lipophilic solvent into the vessel (a) and can be a spike, which is a sharp object designed for penetrating a rubber seal or a rubber stopper. There are spikes on the market which are designed to be virtually safe even in case of improper use, thanks to a kind of "protective wall" around them. Some others have a sheath which must be removed before use.

Alternatively, a suitable connector is the one which can lock the two components (a) and (b) without the use of spikes, usually by means of a thread. Connectors usually have cover caps that need to be removed before operating. In spite of a more complex handling compared to spikes, connectors offer an unbeatable stability of connection together with extreme safety.

Any of the above mentioned connectors device can be used as the means (c) of the invention, provided they are made of materials which are compatible with lipophilic solvent.

By "materials compatible with lipophilic solvents" is meant, according to the present invention, any material that does not interact with said solvents, particularly, does not release any substance toxic to human and/or animal organisms in the lipophilic solvent, and thus in the fluid to be administered. For example, conventional PVC, i.e. containing phthalates that can be extracted from lipophilic solvents, has to be avoided, whereas phthalate-free (or with non-extractable phthalates) PVC, polyethylene, polypropylene, and glass can be used, for example. It is understood that the various components (a), (b) and (c) can be also made of materials different from each other, provided that they all are compatible with lipophilic solvents.

According to a preferred embodiment of the invention, the vessel (a) is a collapsible bottle or flask carrying a suitable rubber seal; the dosage unit (b) is a vial comprising tacrolimus in a suitable lipophilic solvent, also carrying a suitable rubber seal; and the means (c) is a connector carrying one spike on each side.

According to this embodiment, the connector (c) is connected to the vessel (a) as a first step; the vial (b) is than inserted into the connector upside down. In so doing, the spikes present on each side of the connector penetrate the rubber seals and open a way for the flowing of the fluids. By applying a delicate pressure to the vessel (a) the liquid flows from said vessel (a) into the vial (b) and as soon as the pressure is released, being the connection air-tight, the content of the vial (b) is thoroughly refluxed into the vessel (a). This procedure can be performed once or more times and the residual volume in the vial as well as the concentration of the drug in said residual volume can be evaluated in each case and for each type of vial, so that the operating procedure can be adapted accordingly.

According to a particularly preferred embodiment, the drug in the vial above is tacrolimus.

According to a further preferred embodiment, the vial above is a 5 to 10 ml vial, more advantageously a 7 ml vial, containing 5 mg of anhydrous tacrolimus dissolved in 1 ml of lipophilic solvent, e.g. in hydrogenated polyoxyethylenated castor oil (HCO-60) and dehydrated alcohol. It has in fact been proved that this specific combination of vial size and tacrolimus content shows a particularly effective washout during the above described procedure.

According to another aspect of the invention, the at least one dosage unit (b) comprising the drug formulated in a lipophilic solvent and the means (c) for delivering said drug to the vessel (a) are assembled in an individual tool, such as a pre-filled syringe. This allows the healthcare staff to save time, and operate under more comfortable and safer conditions, as it avoids accidental injuries when the ampoules or other dosage units are being opened, and is particularly useful for example with highly active drugs, such as immunosuppressors, antitumoral agents, hormones, etc.

Therefore, according to another of its aspects, the subject-matter of the present invention is a kit for the parenteral administration of formulated drugs in lipophilic solvents, comprising:
  a) at least one vessel containing a fluid for parenteral infusion;
  b') at least one pre-filled syringe comprising at least one drug formulated in a lipophilic solvent to be administered by the parenteral route;
the vessel (a) and the pre-filled syringe (b') being made of materials compatible with lipophilic solvents.

The kits of the invention can also advantageously comprise disposable gloves and an information leaflet, as well as labels reporting the instructions addressed to the healthcare operator.

The pre-filled syringe (b') is, for example, advantageously made of glass, polyethylene or polypropylene, provided with a stopper, preferably made of rubber. Preferably, disposable syringes will be used, with safety needles, that can be advantageously used with one hand, and are already known per se in the art.

According to a preferred aspect of the invention, the drug formulated in a lipophilic solvent is a highly active drug and is selected in the group consisting of tacrolimus, cyclosporine, taxanes (e.g., paclitaxel and docetaxel), alkylating agents such as carmustine and busulfan, teniposide, and valrubicin.

According to another embodiment, the vessel (a) is directly equipped with connectors and tools required for said intravenous infusion, the assembly being made of materials compatible with lipophilic solvents, as stated above.

The fluid for parenteral infusion contained in the vessel (a) must be compatible with the drug in the lipophilic solvent. For example, in the event of drugs that do not tolerate infusion solutions at particular pHs or containing specific carriers, the fluid for parenteral infusion will be suitably selected in order to avoid that the active ingredient may undergo any degradation or alteration.

The fluid for parenteral infusion is a solution for intravenous infusion and contains typically a 0.9% sodium chloride (saline) or a 5% dextrose injection solution. Several active ingredients, such as carmustine or docetaxel require to be pre-diluted in a suitable solvent before they are delivered to the infusion vessel; the solvent is generally provided within the drug package in a separate container, such as ampoules, vials, etc.

The kit of the invention may be adapted to a particular drug, thus comprising also the solvent required therefor and the means for carrying out pre-dilution, said adapted kit still being encompassed by the scope of protection of the present invention.

According to a specific embodiment of the invention, the solvent for the pre-dilution may preferably be provided in a glass vial, rather than in an ampoule, and the kit of the invention can further comprise:

a solvent containing vial for pre-dilution; and
means for carrying out said pre-dilution.

Alternatively, said solvent containing vial for pre-dilution and said means for carrying out said pre-dilution are combined in a pre-filled syringe.

According to a specific embodiment, the solvent for the pre-dilution may preferably be provided in a vial, rather than in an ampoule, and the kit of the invention can further comprise:
- a solvent containing vial for pre-dilution;
- a connector with spike on one side and luer lock on the other; and
- a needle free syringe for the transfer of the solvent.

According to another embodiment of the invention, the kit comprises two vessels (a), the one containing the saline and the other a glucose solution, as described above. This variant allows a healthcare operator to select the infusion solution that is most useful for the treatment at that time.

It is thus understood that the kit of the invention allows completely eliminating the risks involved with the use of vessel for parenteral infusion that are made of materials incompatible with lipophilic solvents in which many drugs are carried, and thereby the risk of administering toxic agents to the patient receiving the infusion is reduced to zero.

In addition, the invention facilitates the task of healthcare staff, on the one hand as it eliminates the risk of using materials incompatible with the specifics used, on the other hand, when using the kit comprising the vessel (a) and syringe (b'), as it eliminates the risk of being injured while opening the dosage units, particularly when the latter are glass ampoules, and further reducing to zero the risk of contamination to staff, when they are deputed to the administration of highly active drugs.

The drug formulated in a lipophilic solvent according to the invention is preferably tacrolimus.

According to a particularly preferred aspect, the subject-matter of the invention is a kit for intravenous administration of tacrolimus, comprising:
- a) at least one vessel containing a fluid for intravenous infusion;
- b") at least one pre-filled syringe comprising tacrolimus in a lipophilic medium;

the vessel (a') and the pre-filled syringe (b") being made of materials compatible with lipophilic solvents.

The vessel (a') is advantageously a glass bottle or bag made of a plastic material other than conventional PVC, such as PE and contains a saline or glucose solution as described above.

The pre-filled syringe advantageously contains 1 ml of a 5 mg solution of anhydrous tacrolimus and 200 mg hydrogenated polyoxyethylenated castor oil (HCO-60) in dehydrated alcohol (for instance, in dehydrated alcohol USP 80% v/v).

The kit of the invention can also be used when there is a direct incompatibility between the PVC and the drug, such as in the case of highly lipophilic active ingredients or drugs encapsulated in liposomes or the like, or still when the active ingredient is absorbed by the PVC of the medical or surgical devices for injection and infusion, such as in the case of pentamidine and tacrolimus.

Therefore, according to another aspect of the invention, the subject-matter of the invention is a kit for the parenteral, advantageously intravenous, administration of PVC-incompatible drugs, comprising:
- a) at least one vessel containing a fluid for parenteral infusion;
- b''') at least one dosage unit comprising at least one PVC-incompatible drug to be administered by the parenteral route;
- c) at least one means for delivering the drug from the dosage unit (b) to the vessel (a);

the vessel (a), dosage unit (b''') and means (c) being made of materials other than PVC.

As described above, the at least one dosage unit (b''') comprising the formulated PVC-incompatible drug, and the means (c) for delivering said drug to the vessel (a) are assembled in an individual tool, such as a pre-filled syringe.

Advantageously, the kit is provided for intravenous infusion.

An example of a PVC-incompatible drug is a highly lipophilic drug; another example of a PVC-incompatible drug is pentamidine or tacrolimus.

The invention is now described by means of examples by way of non-limiting illustration.

EXAMPLES

Example 1

Kit for Intravenous Administration of Tacrolimus

A kit in the form of a pharmaceutical package is prepared comprising
- a bag for intravenous infusion containing 500 ml of a 0.9% sodium chloride saline, connector and butterfly needle, the whole being made of PE;
- a pre-filled syringe containing 1 ml of a 5 mg solution of anhydrous tacrolimus and 200 mg hydrogenated polyoxyethylenated castor oil (HCO-60) in dehydrated alcohol (USP 80% v/v), the syringe being made of materials compatible with lipophilic solvents;
- disposable gloves for pharmaceutical use;
- an information leaflet relating to the active ingredient (tacrolimus).

Example 2

Kit for Intravenous Administration of Tacrolimus

A kit in the form of a pharmaceutical package is prepared comprising
- a PE bag for intravenous infusion containing 300 ml of a 0.9% sodium chloride saline;
- a PE bag for intravenous infusion containing 300 ml of a glucose solution (5% dextrose);
- connector and butterfly needle, the whole being made of materials compatible with lipophilic solvents;
- a pre-filled syringe containing 1 ml of a 5 mg solution of anhydrous tacrolimus and 200 mg hydrogenated polyoxyethylenated castor oil (HCO-60) in dehydrated alcohol (USP 80% v/v), the syringe being made of materials compatible with lipophilic solvents;
- disposable gloves for pharmaceutical use;
- an information leaflet relating to the active ingredient (tacrolimus).

Example 3

Kit for Intravenous Administration of Cyclosporine

A kit in the form of a pharmaceutical package is prepared comprising
- a PE bag for intravenous infusion containing 400 ml of a 0.9% sodium chloride saline, connector and butterfly needle, the whole being made of materials compatible with lipophilic solvents;

a pre-filled syringe made of glass containing 5 ml of a 250 mg cyclosporine solution in 94% (w/w) ethanol and Cremophor EL (polyoxyethylenated castor oil), the syringe being made of materials compatible with lipophilic solvents;

disposable gloves for pharmaceutical use;

an information leaflet relating to the active ingredient (cyclosporine).

Example 4

Kit for Intravenous Administration of Tacrolimus

A kit in the form of a pharmaceutical package is prepared comprising a collapsible tank for intravenous infusion containing 500 ml of a 0.9% sodium chloride saline, carrying a rubber seal, the whole made of materials compatible with lipophilic solvents;

a 7 ml glass vial containing 1 ml of a 5 mg solution of anhydrous tacrolimus and 200 mg hydrogenated polyoxyethylenated castor oil (HCO-60) in dehydrated alcohol (USP 80% v/v), carrying a rubber seal;

a connector carrying one spike on each side, the whole made of materials compatible with lipophilic solvents;

disposable gloves for pharmaceutical use;

an information leaflet relating to the active ingredient (tacrolimus) and to the operating procedure;

Example 5

Kit for Intravenous Administration of Docetaxel

A kit in the form of a pharmaceutical package is prepared comprising:

For the pre-dilution:

a glass vial containing 6 ml of 13% ethanol solution in water for Injection, as pre-dilution solvent;

a needle free syringe for the transfer of the solvent;

a connector with spike on one side and luer lock on the other for the pre-dilution.

For the preparation of the infusion to be administered:

a collapsible flask for intravenous infusion containing 500 ml of a 0.9% sodium chloride saline, carrying a rubber seal, the whole made of materials compatible with lipophilic solvents;

a 10 ml glass vial containing 80 mg docetaxel in 2 ml polysorbate 80; carrying a rubber seal;

a connector carrying one spike on each side for the transfer, the whole made of materials compatible with lipophilic solvents;

disposable gloves for pharmaceutical use;

the kit also comprising an information leaflet relating to the active ingredient (docetaxel) and to the operating procedure for administration.

The invention claimed is:

1. A pharmaceutical package comprising a kit for parenteral intravenous infusion of drugs formulated in lipophilic solvents, the kit comprising:

a) at least one vessel containing a solution for intravenous infusion that is selected from a saline and a glucose solution; and b) a pre-filled syringe containing a solution of 1 ml of a 5 mg solution of anhydrous tacrolimus and 200 mg hydrogenated polyoxyethylenated castor oil (HCO-60) in dehydrated alcohol (USP 80% v/v), said pre-filled syringe comprising means for delivering the solution to said at least one vessel;

the vessel (a), and pre-filled syringe being made of materials compatible with lipophilic solvents.

2. The pharmaceutical package according to claim 1, characterized in that said materials compatible with lipophilic solvents are other than conventional PVC.

3. The pharmaceutical package according to claim 1, characterized in that said materials compatible with lipophilic solvents are selected from glass, polyethylene, polypropylene and PVC free of any phthalates that may be released in lipophilic solvents.

4. The pharmaceutical package according to claim 1, characterized in that said vessel (a), and pre-filled syringe (b) are made of either the same or different materials.

5. The pharmaceutical package according to claim 1, characterized in that said vessel (a) also comprises optional connectors, cannulae, flow regulators, filters and/or dosers.

6. The pharmaceutical package according to claim 1, characterized in that it comprises two vessels (a).

7. The pharmaceutical package according to claim 1, further comprising disposable gloves and an information leaflet.

* * * * *